United States Patent [19]

Wals et al.

[11] Patent Number: 4,898,873

[45] Date of Patent: * Feb. 6, 1990

[54] α,α-DIARYL-4-ARYL-4-HYDROXYL-1-PIPERIDINEBUTANAMIDE, N-OXIDES AND PHARMACEUTICAL USE

[75] Inventors: Lourens Wals, Turnhout; Ludwig P. Cooymans, Beerse, both of Belgium

[73] Assignee: Janssen Pharmaceutica N.V., Beerse, Belgium

[*] Notice: The portion of the term of this patent subsequent to Apr. 25, 2006 has been disclaimed.

[21] Appl. No.: 294,541

[22] Filed: Jan. 9, 1989

Related U.S. Application Data

[63] Continuation of Ser. No. 888,606, Jul. 23, 1986, Pat. No. 4,824,853, and a continuation-in-part of Ser. No. 786,566, Oct. 11, 1985, abandoned.

[51] Int. Cl.$^4$ .................. A61K 31/445; C07D 211/94
[52] U.S. Cl. ..................................... 514/327; 546/217
[58] Field of Search ......................... 546/217; 514/327

[56] References Cited

U.S. PATENT DOCUMENTS

| | | | |
|---|---|---|---|
| 3,714,159 | 1/1973 | Janssen et al. | 546/189 |
| 3,843,646 | 10/1974 | Kreider | 514/867 |
| 3,892,776 | 7/1975 | Hook et al. | 514/866 |
| 4,086,345 | 4/1978 | Garzia et al. | 514/249 |
| 4,277,605 | 7/1981 | Buyniski et al. | 514/867 |
| 4,306,069 | 12/1981 | Lawson | 546/234 |

OTHER PUBLICATIONS

M. H. Bickel, "The Pharmacology and Biochemistry of N-Oxides" (1969), Pharmacological Reviews, vol. 21, No. 4, pp. 325–355.

Carlos J. E. Niemegeers et al., Drug Development Research, vol. 8 (1986), pp. 279–286.

K. D. Stahl et al., European Journal of Pharmacology, vol. 46 (1977), pp. 199–205.

Primary Examiner—Richard L. Raymond

[57] ABSTRACT

Antidiarrheal active α,α-diaryl-4-aryl-4-hydroxy-1-piperidinebutanamide, N-oxides, compositions containing the same and methods of treating diarrhea.

3 Claims, No Drawings

α,α-DIARYL-4-ARYL-4-HYDROXYL-1-PIPERIDINEBUTANAMIDE, N-OXIDES AND PHARMACEUTICAL USE

This is a continuation of of application Ser. No. 888,606, filed July 23, 1986, now U.S. Pat. No. 4,824,853, which is a continuation-in-part of our co-pending application Ser. No. 786,566, filed Oct. 11, 1985, now abandoned.

BACKGROUND OF THE INVENTION

In U.S. Pat. No. 3,714,159, there are described 2,2-diaryl-4-(4'-hydroxy-piperidino)-butyramides which compounds are taught to possess useful antidiarrheal and analgesic activities. The compounds of the present invention differ therefrom by the fact that they invariably contain a 1-piperidine oxide moiety and by their improved pharmacological properties.

DESCRIPTION OF THE PREFERRED EMBODIMENTS

The present invention is concerned with novel α,α-diaryl-4-aryl-4-hydroxy-1-piperidinebutanamide, N-oxides which may structurally be represented by the formula:

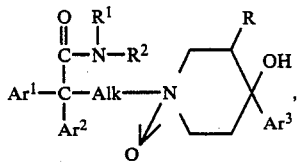

(I)

the pharmaceutically acceptable acid addition salts and stereochemically isomeric forms thereof, wherein
R is hydrogen or methyl;
$Ar^1$ and $Ar^2$ are, each independently, phenyl or halophenyl;
Alk is $-CH_2-CH_2-$ or $-CH_2-CH(CH_3)-$;
$R^1$ and $R^2$ are, each independently, hydrogen, $C_{1-6}$alkyl, phenylmethyl or 2-propenyl or $R^1$ and $R^2$ combined with the nitrogen atom bearing said $R^1$ and $R^2$ may form a pyrrolidinyl, piperidinyl, $C_{1-6}$alkylpiperidinyl, 4-morpholinyl or 2,6-di($C_{1-6}$alkyl)-4-morpholinyl radical;
$Ar^3$ is phenyl being optionally substituted with up to 3 substituents selected from the group consisting of $C_{1-6}$alkyl, $C_{1-6}$alkyloxy, halo and trifluoromethyl.

As used in the foregoing definitions the term halo is generic to fluoro, chloro, bromo and iodo: "$C_{1-6}$alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like.

Preferred compounds within the invention are those wherein $R^1$ and $R^2$ are both methyl and $Ar^1$ and $Ar^2$ are both phenyl.

Particularly preferred compounds are those preferred compounds wherein $Ar^3$ is phenyl being optionally substituted with one or two substituents independently selected from halo and trifluoromethyl.

More particularly preferred compounds within the invention are selected from the group consisting of 4-(4-chlorophenyl)-4-hydroxy-N,N-dimethyl-α,α-diphenyl-1-piperidinebutanamide, N-oxide, the pharmaceutically acceptable acid addition salts and stereoisomeric forms thereof.

The most preferred compounds within the invention are selected from the group consisting of trans-4-(4-chlorophenyl)-4-hydroxy-N,N-dimethyl-α,α-diphenyl-1-piperidinebutanamide, N-oxide and the pharmaceutically acceptable acid addition salts thereof.

The compounds of formula (I) may generally be prepared by N-oxidating a starting material of formula

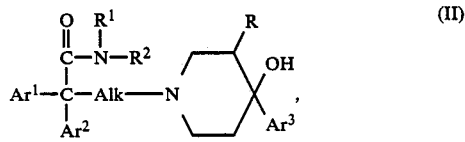

(II)

said N-oxidation reaction may generally be carried out by reacting the starting material of formula (II) with an appropriate organic or inorganic peroxide. Appropriate inorganic peroxides comprise, for example, hydrogen peroxide, alkali metal or earth alkaline metal peroxides, e.g. sodium peroxide, potassium peroxide, barium peroxide and the like; appropriate organic peroxides may comprise peroxy acids such as, for example, benzenecarboperoxoic acid or halo substituted benzenecarbo-peroxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. Suitable solvents are, for example, water, lower alkanols, e.g. methanol, ethanol, propanol, butanol and the like, hydrocarbons, e.g. benzene, methylbenzene, dimethylbenzene and the like, ketones, e.g. 2-propanone, 2-butanone and the like, halogenated hydrocarbons, e.g. dichloromethane, trichloromethane and the like, and mixtures of such solvents. In order to enhance the reaction rate, it may be appropriate to heat the reaction mixture.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 2-hydroxybenzoic, 3-phenyl-2-propenoic, α-hydroxybenzeneacetic, 4-amino-2-hydroxybenzoic and the like acids. Conversely the salt form can be converted by treatment with alkali into the free base form.

The intermediates of formula (II) are known compounds and can be prepared according to the procedures described in U.S. Pat. No. 3,714,159.

From formula (I) it is evident that the compounds of this invention may have several asymmetric carbon atoms in their structure. Each of these chiral centers may be present in a R- and a S-configuration, this R- and S-notation being in correspondence with the rules described in J. Org. Chem., 35, 2849–2867 (1970).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

In some compounds and starting materials the stereochemical configuration is not experimentally determined. In those cases it is conventionally agreed to designate the stereochemically isomeric form which is first isolated as "A" and the second as "B", without further reference to the actual stereochemical configuration.

The compounds of formula (I), their pharmaceutically acceptable acid-addition salts and stereoisomeric forms possess useful pharmacological properties. They show antidiarrheal activity, which activity is evidenced by the experimental data obtained in, for example, the "Castor Oil Test in Rats".

The compounds of formula (I), their pharmaceutically acceptable acid-addition salts and stereoisomeric forms are particularly attractive due to the strongly decreased central effects as compared with the prior-art compounds of U.S. Pat. No. 3,714,159. This can be demonstrated by the results of, for example, the "Tail Withdrawal Test in Rats" which can be considered as an indicator for the occurrence of central effects. The compounds of the present invention are also attractive due to their favourable toxicity, particularly when compared to the toxicity of the prior-art compounds of U.S. Pat. No. 3,714,159.

Due to their useful pharmacological properties the compounds of formula (I), their pharmaceutically acceptable acid addition salts and stereoisomeric forms can be used in the treatment of diarrhea.

Due to the absence of undesired central effects, they are particularly useful in the treatment of diarrhea in subjects where medicines having said undesired central effects can be harmful, for example, in the treatment of children and infants.

In view of their useful antidiarrheal properties, the subject compounds may be formulated into various pharmaceutical forms for administration purposes.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salt of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of diarrhea, it is evident that the present invention provides a method of treating warm-blooded animals suffering from diarrhea, said method comprising the systemic administration of a pharmaceutically effective amount of a compound of formula (I), a pharmaceutically acceptable acid-addition salt or stereoisomeric form thereof.

Those of skill in treating warm-blooded animals suffering from diarrhea could easily determine the effective amount from the test results presented here. In general it is contemplated that an effective amount would be from 0.001 mg/kg to 20 mg/kg body weight, preferably from 0.005 mg/kg to 5 mg/kg body weight and more preferably from 0.01 to 0.1 mg/kg body weight.

The following examples are intended to illustrate and not to limit the scope of the present invention. Unless otherwise stated all parts therein are by weight.

EXAMPLES (A) Preparation of Final Compounds

Example 1

A mixture of 26.5 parts of 4-(4-chlorophenyl)-4-hydroxy-N,N-dimethyl-$\alpha,\alpha$-diphenyl-1-piperidinebutanamide, 17.1 parts of a hydrogen peroxide solution 30%, 200 parts of methanol and 315 parts of methylbenzene was stirred first for 20 hours at 60° C. and then for 96 hours at 70° C. The reaction mixture was evaporated. The residue was purified by column-chromatography (HPLC) over silica gel using a mixture of trichloromethane, methanol and methanol, saturated with ammonia, (90:9:1 by volume) as eluent. The pure fractions were collected and the eluent was evaporated. The residue was crystallized from a mixture of 2,2'-oxybispropane and a small amount of methanol. The product was filtered off and dried in a dry-pistol with methylbenzene for 30 minutes at reflux temperature, yielding 2.0 parts (7%) of trans-4-(4-chlorophenyl)-4-hydroxy-N,N-dimethyl-α,α-diphenyl-1-piperidinebutanamide. N-oxide; mp. 149.7° C. (1).

Example 2

A mixture of 21.5 parts of 4-[4-chloro-3-(trifluoromethyl)phenyl]-4-hydroxy-N,N-dimethyl-α,α-diphenyl-1-piperidinebutanamide, 8.6 parts of a hydrogen peroxide solution 30% and 260 parts of 4-methyl-2-pentanone was stirred for 24 hours at 80° C. After cooling in an ice-bath, the precipitated product was filtered off and dried, yielding 10.4 parts (46%) of (A)-4-[4-chloro-3-(trifluoromethyl)phenyl]-4-hydroxy-N,N-dimethyl-α,α-diphenyl-1-piperidinebutanamide, N-oxide; mp. 185.3° C. (2).

Example 3

A mixture of 20 parts of 4-[4-chloro-3-(trifluoromethyl)phenyl]-4-hydroxy-N,N-dimethyl-α,α-diphenyl-1-piperidinebutanamide, 8 parts of a hydrogen peroxide solution 30% and 240 parts of 4-methyl-2-pentanone was stirred for 24 hours at 80° C. The reaction mixture was cooled in an ice bath. The precipitated product was filtered off and the filtrate was evaporated. The residue was purified by column chromatography over silica gel using a mixture of trichloromethane and methanol (90:10 by volume) as eluent. The second fraction was collected and the eluent was evaporated. The residue was further purified by column chromatography (HPLC) over silica gel using a mixture of hexane, trichloromethane, methanol and ammonium hydroxide (45:50:5:0.05 by volume) as eluent. The pure fractions were collected and the eluent was evaporated. The residue was stirred in 2,2'-oxybispropane. The product was filtered off and dried, yielding 1.2 parts of (B)-4-[4-chloro-3-(trifluoromethyl)phenyl]-4-hydroxy-N,N-dimethyl-α,α-diphenyl-1-piperidinebutanamide, N-oxide sesquihydrate; mp. 152.9° C. (3).

Example 4

To a stirred solution of 133.0 parts of 4-(4-chlorophenyl)-4-hydroxy-N,N-dimethyl-α,α-diphenyl-1-piperidinebutanamide in 2000 parts of 4-methyl-2-pentanone were added 57.0 parts of a hydrogen peroxide solution 30%. The whole was stirred for 20 hours at 80° C. After cooling overnight, the precipitate was filtered off (filtrate I was set aside) and boiled in 4-methyl-2-pentanone. The undissolved part was filtered off and the filtrate, together with filtrate I, was evaporated. The residue was purified by column chromatography over silica gel using a mixture of trichloromethane and methanol (90:10 by volume) as eluent. The second fraction was collected and the eluent was evaporated. The residue was purified twice: first by column chromatography over silica gel using a mixture of trichloromethane, methanol and ammonium hydroxide (90:9:1 by volume) as eluent and then by column chromatography (HPLC) over silica gel using a mixture of trichloromethane, hexane, methanol and methanol, saturated with ammonia, (45:45:9:1 by volume) as eluent. The pure fractions were collected and the eluent was evaporated. The residue was stirred in 2,2'-oxybispropane. The product was filtered off and dried, yielding 2.3 parts of cis-4-(4-chlorophenyl)-4-hydroxy-N,N-dimethyl-α,α-diphenyl-1-piperidinebutanamide, N-oxide; mp. 146.6° C. (4).

In a similar manner there are also prepared:

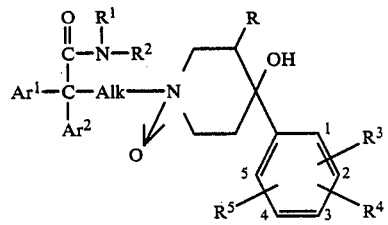

| No. | Ar¹ | Ar² | R | R¹ | R² | R³ | R⁴ | R⁵ | Alk |
|-----|-----|-----|---|----|----|----|----|----|-----|
| 5 | C₆H₅ | C₆H₅ | H | | (CH₂)₄ | 3-Cl | H | H | (CH₂)₂ |
| 6 | C₆H₅ | C₆H₅ | H | | (CH₂)₂—O—(CH₂)₂ | 3-Cl | H | H | (CH₂)₂ |
| 7 | C₆H₅ | C₆H₅ | H | | (CH₂)₅ | 2-CF₃ | 3-Cl | H | (CH₂)₂ |
| 8 | C₆H₅ | C₆H₅ | H | C₂H₅ | C₂H₅ | 2-CF₃ | 3-Cl | H | (CH₂)₂ |
| 9 | C₆H₅ | C₆H₅ | H | | (CH₂)₂—O—(CH₂)₂ | 3-CH₃ | H | H | (CH₂)₂ |
| 10 | C₆H₅ | C₆H₅ | H | C₂H₅ | C₂H₅ | 3-F | H | H | (CH₂)₂ |
| 11 | C₆H₅ | C₆H₅ | H | CH₃ | CH₃ | H | H | H | CH₂—CH(CH₃) |
| 12 | C₆H₅ | C₆H₅ | H | CH₃ | CH₃ | 3-Br | H | H | (CH₂)₂ |
| 13 | C₆H₅ | C₆H₅ | H | | (CH₂)₄ | 2-Cl | 3-Cl | H | (CH₂)₂ |
| 14 | C₆H₅ | C₆H₅ | H | C₃H₇ | C₃H₇ | 3-Cl | H | H | (CH₂)₂ |
| 15 | C₆H₅ | C₆H₅ | H | C₄H₁₁ | C₄H₁₁ | 3-Cl | H | H | (CH₂)₂ |
| 16 | C₆H₅ | C₆H₅ | H | | CH₂—CH—O—CH—CH₂<br>       \|            \|<br>      CH₃        CH₃ | 3-Cl | H | H | (CH₂)₂ |
| 17 | C₆H₅ | C₆H₅ | H | CH₃ | CH₃ | 1-CH₃ | 1-CH₃ | H | (CH₂)₂ |
| 18 | C₆H₅ | C₆H₅ | H | | (CH₂)₂—C—(CH₂)₂<br>          \|<br>         CH₃ | 3-Cl | H | H | (CH₂)₂ |
| 19 | C₆H₅ | C₆H₅ | H | C₂H₅ | CH₃ | 3-Cl | H | H | (CH₂)₂ |
| 20 | C₆H₅ | C₆H₅ | H | | CH₂—CH—(CH₂)₃<br>          \|<br>         CH₃ | 3-Cl | H | H | (CH₂)₂ |
| 21 | C₆H₅ | C₆H₅ | H | CH₃ | CH₂—C₆H₅ | 3-Cl | H | H | (CH₂)₂ |

-continued

| No. | Ar$^1$ | Ar$^2$ | R | R$^1$ | R$^2$ | R$^3$ | R$^4$ | R$^5$ | Alk |
|---|---|---|---|---|---|---|---|---|---|
| 22 | C$_6$H$_5$ | C$_6$H$_5$ | CH$_3$ | CH$_3$ | CH$_3$ | 2-CF$_3$ | 3-Cl | H | (CH$_2$)$_2$ |
| 23 | C$_6$H$_5$ | C$_6$H$_5$ | H | CH$_3$ | CH$_3$ | 2-CH$_3$ | 3-CH$_3$ | 4-CH$_3$ | (CH$_2$)$_2$ |
| 24 | C$_6$H$_5$ | C$_6$H$_5$ | H | CH$_2$—CH=CH$_2$/CH$_2$—CH=CH$_2$ | | 3-Cl | H | H | (CH$_2$)$_2$ |
| 25 | C$_6$H$_5$ | C$_6$H$_5$ | H | CH$_3$ | C$_3$H$_7$ | 3-Cl | H | H | (CH$_2$)$_2$ |
| 26 | C$_6$H$_5$ | C$_6$H$_5$ | CH$_3$ | CH$_3$ | CH$_3$ | 2-CF$_3$ | H | H | (CH$_2$)$_2$ |
| 27 | C$_6$H$_5$ | C$_6$H$_5$ | H | CH$_3$ | i-C$_3$H$_7$ | 3-Cl | H | H | (CH$_2$)$_2$ |
| 28 | C$_6$H$_5$ | C$_6$H$_5$ | H | CH$_3$ | CH$_3$ | 1-OCH$_3$ | 4-OCH$_3$ | H | (CH$_2$)$_2$ |
| 29 | 3FC$_6$H$_4$ | 3FC$_6$H$_5$ | H | CH$_3$ | CH$_3$ | 3-Cl | H | H | (CH$_2$)$_2$ |
| 30 | 3FC$_6$H$_4$ | C$_6$H$_5$ | H | CH$_3$ | CH$_3$ | 3-Cl | H | H | (CH$_2$)$_2$ |
| 31 | 3FC$_6$H$_4$ | 3ClC$_6$H$_4$ | H | CH$_3$ | CH$_3$ | 3-Cl | H | H | (CH$_2$)$_2$ |
| 32 | C$_6$H$_5$ | C$_6$H$_5$ | H | H | CH$_3$ | 3-Cl | H | H | (CH$_2$)$_2$ |
| 33 | C$_6$H$_5$ | C$_6$H$_5$ | H | H | H | 3-Cl | H | H | (CH$_2$)$_2$ |
| 34 | C$_6$H$_5$ | C$_6$H$_5$ | H | CH$_3$ | CH$_3$ | 2-CF$_3$ | 3-Cl | H | CH(CH$_3$)—CH$_2$ |

(B) Pharmacological Examples

Example 5

Castor Oil Test in Rats

Female Wistar rats were fasted overnight. Each animal was treated intravenously with the desired dose of the compound to be tested. One hour thereafter, the animal received 1 ml of castor oil orally. Each animal was kept in an individual cage and 2 hours after the castor oil treatment, the presence or absence of diarrhea was noted. The ED$_{50}$ value was determined as that dose in mg/kg body weight, at which no diarrhea was present in 50% of the tested animals. Said ED$_{50}$-value for a compound of the present invention and for 4-(4-chlorophenyl)-4-hydroxy-N,N-dimethyl-α,α-diphenyl-1-piperidinebutanamide, which compound is generically designated as loperamide and which is described in U.S. Pat. No. 3,714,159, can be found in table I.

Example 6

Tail Withdrawal Test in Rats

Female Wistar rats were fasted overnight. Each animal was treated intravenously with the desired dose of the compound to be tested. The thus treated rats were put into individual restraining cages. After the administration of the test compound, the lower 5 cm portion of the tail was immersed into a cup filled with water at a constant temperature of 55° C. The typical tail withdrawal response was evaluated during a 10 seconds period after the immersion. ED$_{50}$ values in mg/kg body weight were determined as that dose of the test compound capable of suppressing in 50% of the tested animals the typical tail withdrawal response during a time period exceeding 10 seconds. Said ED$_{50}$ values obtained for a compound of the present invention and for 4-(4-chlorophenyl)-4-hydroxy-N,N-dimethyl-α,α-diphenyl-1-piperidinebutanamide (i.e. loperamide) are also gathered in table I. From these ED$_{50}$-values, it can be concluded that the prior art compound antagonizes the typical tail withdrawal reflex, while the compound 1 does not show such activity.

Example 7

Determination of toxicity

Female Wistar rats were treated with the compound to be tested at various dose levels. LD$_{50}$ values were determined as that dose in mg/kg body weight being lethal in 50% of the tested animals. Said LD$_{50}$ values obtained for a compound of the present invention and for 4-(4-chlorophenyl)-4-hydroxy-N,N-dimethyl-α,α-diphenyl-1-piperidinebutanamide (i.e. loperamide) are also listed in table I. From these values it can be concluded that the compounds of the present invention show a decreased toxicity.

Example 8

Determination of the safety margin and antidiarrheal specificity

The safety margin for the antidiarrheal action was determined as the ratio of the LD$_{50}$ value to the ED$_{50}$ value obtained in the Castor Oil Test. The antidiarrheal specificity was determined as the ratio of the ED$_{50}$ value obtained in the Tail Withdrawal Test to the ED$_{50}$ value obtained in the Castor Oil Test. These values are also listed in table I. Both the safety margin for the antidiarrheal action and the antidiarrheal specificity of the compounds of the present invention are superior to the same of the prior-art compound.

TABLE I

| Compound no. | Castor Oil ED$_{50}$ in mg/kg | Tail Withdrawal ED$_{50}$ in mg/kg | LD$_{50}$ | Safety Margin antidiarrheal | Antidiarrheal specificity |
|---|---|---|---|---|---|
| * | 0.095 | 2.83 | 5.92 | 62.3 | 29.8 |
| 1 | 0.21 | >20.0 | 28.3 | 135 | >95 |

*loperamide (C) COMPOSITION EXAMPLES

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or pharmaceutically acceptable acid addition salt thereof.

Example 9: ORAL DROPS

500 Grams of the A.I. was dissolved in 0.5 liters of 2-hydroxypropanoic acid and 1.5 liters of the polyethylene glycol at 60°–80° C. After cooling to 30°–40° C. there was added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 10: ORAL SOLUTION

9 Grams of methyl 4-hydroxybenzoate and 1 gram of propyl 4-hydroxybenzoate was dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 11: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 12: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

Example 13: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.

The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 14: SUPPOSITORIES

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°-38° C. to form 100 suppositories each containing 30 milligrams of the active ingredient.

What is claimed is:

1. The compound 4-[4-chloro-3-(trifluoromethyl)-phenyl]-4-hydroxy-N,N-dimethyl-α,α-diphenyl-1-piperidinebutaneamide, N-oxide.

2. A composition comprising suitable pharmaceutical carriers and as active ingredient an anti-diarrheal effective amount of the compound 4-[4-chloro-3-(trifluoromethyl)phenyl]-4-hydroxy-N,N-dimethyl-α,α-diphenyl-1-piperidinebutaneamide, N-oxide.

3. A method of treating warm-blooded animals suffering from diarrhea, which method comprises the systemic administration to warm-blooded animals of an effective anti-diarrheal amount of the compound 4-[4-chloro-3-(trifluoromethyl)phenyl]-4-hydroxy-N,N-dimethyl-α,α-diphenyl-1-piperidine-butaneamide, N-oxide.

* * * * *